(12) United States Patent
Lee

(10) Patent No.: US 8,877,434 B2
(45) Date of Patent: Nov. 4, 2014

(54) METHOD AND SYSTEM OF DETECTING DIOXIN-LIKE COMPOUNDS

(76) Inventor: Hsinyu Lee, San Diego, CA (US)

(*) Notice: Subject to any disclaimer, the term of this patent is extended or adjusted under 35 U.S.C. 154(b) by 0 days.

(21) Appl. No.: 13/451,498

(22) Filed: Apr. 19, 2012

(65) Prior Publication Data

US 2013/0280741 A1 Oct. 24, 2013

(51) Int. Cl.
*C12Q 1/00* (2006.01)
*C12Q 1/66* (2006.01)

(52) U.S. Cl.
USPC .................................................. 435/4; 435/8

(58) Field of Classification Search
None
See application file for complete search history.

(56) References Cited

U.S. PATENT DOCUMENTS 7,211,399 B2 * 5/2007 Jockers et al.

FOREIGN PATENT DOCUMENTS

WO WO 2005/100991 * 10/2005

OTHER PUBLICATIONS

Lin et al. J. Biomed. Sci. (2008)15, 833-840.*

* cited by examiner

*Primary Examiner* — Nashaat Nashed
(74) *Attorney, Agent, or Firm* — WPAT, P.C.; Anthony King; Kay Yang

(57) ABSTRACT

The invention relates to a method or a cell free system of detecting dioxin-like compounds in a test sample using a whole cell lysate derived from a cell transfected to express a fusion protein comprising an AHR fused to a reporter peptide. The method in combination with bioluminescence resonance energy transfer (BRET) technique is also provided so as to improve the sensitivity.

9 Claims, 7 Drawing Sheets

METHOD AND SYSTEM OF DETECTING DIOXIN-LIKE COMPOUNDS

FIELD OF THE INVENTION

The present invention relates to a method and a system of detecting dioxin-like compounds.

BACKGROUND OF THE INVENTION

Dioxins are normally formed due to incomplete combustion processes and belong to a group of robust and mostly toxic chemical substances known as persistent organic pollutants. Among them, 2,3,7,8-tetrachlorodibenzo-p-dioxin (TCDD) is considered to be the most toxic species and classed as a known carcinogen by the World Health Organization (WHO). The toxicity of the other dioxin species or mixtures of dioxins is normally described in relation to TCDD.

Traditionally, analytical chemical processes, such as chromatographic and mass spectral technologies, are employed to determine the dioxin content in samples. However, these processes are cost-ineffective and time-consuming and, more importantly, the results obtained thereby are not directly correlated to the toxicity of dioxin. All these disadvantages make the analytical chemical processes unsuitable for high throughput screening.

In 1995, the biological effects of dioxins were reported to be mediated by the aryl hydrocarbon receptor (AHR) pathway (Fernandersalguero, et al., Science 268: 722-726, 1995). AHR is a resident protein found in the cytoplasm, which forms a heteromer with two molecules of heat shock protein 90 (HSP90). Dioxin molecules can easily penetrate across the plasma membrane and bind to the heteromer, causing the heteromer to undergo transformation that dissociates AHR from HSP90. The free form of AHR is active to be translocated into the nucleus where it binds to an AHR nuclear translocator (ARNT) protein. The AHR-ARNT complex is proved to be a transcription activator that binds to certain regulatory sequences in DNA, including the so-called dioxin responsive element (DRE), and triggers the expression of downstream effectors. Given the fact that AHR dissociates from HSP90 and then associates with ARNT upon binding to dioxin, a broad variety of bioassays were established in 1990's. For example, Wheelock et al. provided a method of detecting dioxin-like compounds in a test sample (U.S. Pat. No. 5,529,899 filed on Jul. 27, 1993 and issued on Jun. 25, 1996). In this method, the test sample was contacted with a heteromer formed from an inactive AHR. If dioxin-like compounds are present in the test sample, they will bind to the AHR causing it to dissociate from the heteromer as a complex containing active AHR bound to a dioxin-like compound ligand. Then, Wheelock et al. further provided a method of detecting dioxin-like compounds using ARNT to optimize AHR transformation (U.S. Pat. No. 6,127,136 filed on Feb. 14, 2006 and issued on Oct. 3, 2000). Okuyama et al. provided a study on enzyme-linked immunoabsorbent assay (ELISA) using a monoclonal anti-dioxin antibody with a sensitivity at nanomolar level (Okuyama, et al., Anal. Chem. 76: 1948-1956, 2004). However, the above-mentioned methods are dissatisfied because of low sensitivity.

Furthermore, in vitro bioassays based on fluorescence resonance energy transfer (FRET) technique have been developed, which involve assessment of the interactions between AHR and its binding partners to determine the dioxin content in test samples (see, for example, Lin, et al., J. Biomed. Sci. 15: 833-840, 2008; and Lin, et al., Chin. Biosci. 50(1): 12-25, 2007). In this study, a fluorescence resonance energy transfer (FRET)-based dioxin-detection bioassay was established, wherein AHR and ARNT fused-cyan fluorescent protein (CFP) and -yellow fluorescent protein (YFP) constructed were transiently co-transfected into rat hepatoma cell line, H4IIEC3 cells. The results showed that dioxin treatments upregulated FRET signals in the transfected cells in a dose-dependent manner. In spite of the high sensitivity and specificity achieved by these assays, the use of cell-based systems for detecting dioxin-like compounds is less desirable in view of the cumbersome in manipulating living cells and the inherent variability of whole cells.

Recently, a cell-free assay system was provided in WO 2005/100991, where recombinant AHR and ANRT in their partially purified forms were prophetically subjected to FRET analysis. However, no empirical data were shown in this regard.

Therefore, there exists a need for cost-effective and high-throughput methods and cell-free systems to enable rapid and quantitative detection of a dioxin-like compound with high sensitivity.

SUMMARY OF THE INVENTION

It is surprisingly found in the present invention that the whole cell lysate of a cell transfected to express a fusion protein of AHR and a reporter peptide is vulnerable to proteases and will degrade in a dose-dependent manner relative to the concentrations of a dioxin-like compound added. Accordingly, a method for detecting a dioxin-like compound in a test sample in a cell-free system is established by using the whole cell lysate and monitoring the degradation of AHR protein upon the presence of the dioxin-like compound.

In one aspect, the invention provides a method of detecting a dioxin-like compound in a test sample comprising:
providing a whole cell lysate derived from a cell transfected to express one or more fusion proteins fused to a reporter peptide, one of which comprises an AHR, and wherein the whole cell lysate comprises the fusion protein in a dissociated complex;
contacting the test sample with the whole cell lysate for a period of time sufficient for the fusion protein in a dissociated complex to degrade upon the presence of the dioxin-like compound; and
detecting a detectable signal generated by the reporter peptide as indicative of an amount of the fusion protein and comparing to a reference signal generated with a known concentration of a dioxin-like compound, thereby determining the presence or amount of the dioxin-like compound in the test sample.

In another aspect, the invention provides a method for detecting a dioxin-like compound in a test sample in association with bioluminescence resonance energy transfer (BRET) technique, so as to improve the sensitivity.

In further aspect, the invention provides a cell-free system for performing the method for detecting a dioxin-like compound in a test sample according to the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

FIGS. 1A-1D are the restriction maps of the plasmids employed for transfecting the cells according to the invention, wherein FIG. 1A shows the restriction sites of AHR, FIG. 1B shows the restriction sites of AIP and P23, FIG. 1C shows the restriction sites of ARNT and FIG. 1D shows the restriction sites of HSP90.

DETAILED DESCRIPTION OF THE INVENTION

Figure 1A:
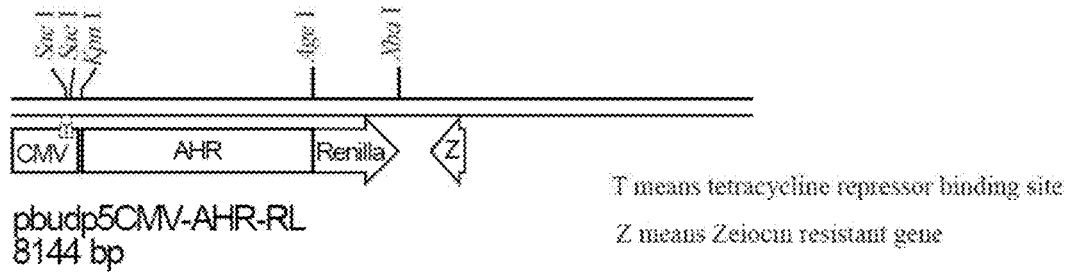

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "dioxins" or "dioxin-like compounds" refers to a family of polyhalogenated aromatic hydrocarbons, including polychlorinated dibenzodioxins, polychlorinated dibenzofurans, polychlorinated biphenyls, and structural analogs thereof that exhibit similar toxicity to dioxin. The dioxin-like compounds may be one or more compounds selected from a chemical family consisting of approximately 210 dioxin derivatives, including 75 species of polychlorinated dibenzo-p-dioxins (PCDDs) and 135 species of polychlorinated dibenzofurans (PCDFs), as described in Hu et al., *J. Toxicol. Environ. Health B Crit. Rev.* 2: 183-210. In one example of the invention, the dioxin-like compound is 2,3,7,8-tetrachlorodibenzo-p-dioxin (TCDD) or 3-methylcholanthrene (3MC). In the invention, the dioxin-like compounds may also be present in the form of a mixture containing more than one dioxin-like compound in a test sample.

As used herein, the term "aryl hydrocarbon receptor," or abbreviated as "AHR," is intended to encompass naturally occurring and recombinant species thereof, as well as functionally equivalent variants or fragments thereof. A functional AHR, when present in its inactive or ligand-free form, is capable of being associated with its binding partners to constitute a heteromer and is prone to dissociate from the heterodimer upon binding to a ligand, such as a dioxin-like compound. The active or ligand-binding form of AHR is in turn bound to ARNT protein.

The term "binding partners" is used herein to encompass all of the molecules, in particular the protein molecules, which are associated with the inactive AHR protein in the heterodimer. The binding partners include but are not limited to heat shock protein 90 (HSP90), AHR-interacting protein (AIP), P23 and other protein molecules present in the heteromer, or combination thereof. In a preferred embodiment, the binding partner is a naturally occurring or recombinant HSP90, or a functionally equivalent variant or fragment thereof. As used herein, the term "AHR nuclear translocator," or abbreviated as "ARNT," is intended to encompass naturally occurring and recombinant species thereof, as well as functionally equivalent variants or fragments thereof. A functional ARNT is capable of binding to the AHR-ligand complex.

The term "reporter peptide" as used herein refers to a peptide tag that is adapted for being fused to AHR, the binding partners thereof, or ARNT to constitute a fusion protein and is capable of being assayed by suitable means, thereby allowing detection of the presence and/or quantity of the fusion protein, or interactions between fusion proteins. In one embodiment, cyan fluorescent protein (CFP) and yellow fluorescent protein (YFP) are employed in the assay as a reporter peptide pair for FRET analysis. In another embodiment, a bioluminescent luciferase, preferably *Renilla* luciferase (RL), is cooperatively used with YFP in the assay as a reporter peptide pair for BRET analysis. In a preferred embodiment, *Renilla* luciferase (RL) is employed in the assay in conjunction with coelenterazine as a catalytic substrate, wherein the substrate is oxidized through the enzymatic catalyzation to emit luminescent light.

The term "whole cell lysate" as used herein refers to nonviable cell suspensions obtained by lyzing the cells which produce natural or recombinant forms of one or more of the proteins required for carrying out the assay. According to the invention, the whole cell lysate is derived from a cell that is genetically engineered to express AHR fused to a reporter peptide. Furthermore, one or more of its binding partners such as HSP90, or ARNT may be used. In one embodiment of the invention, the whole cell lysate is derived from a cell that is genetically engineered to co-express AHR and HSP90. In a particular example of the invention, the cells were prepared to co-express the AHR fused to RL, AIP, P23 and HSP90 fused to YFP, called as "AAPH cells." In another embodiment of the invention, the whole cell lysate is derived from a cell that is genetically engineered to co-expresses AHR and ARNT. In a particular example of the invention, the cells were prepared to co-express the AHR fused to RL, AIP, P23 and ARNT fused to YFP, called as "AAPA cells." Preferably, AIP may be a His-tagged AIP and P23 may be a His-tagged P23. In addition, the cells used in the invention may be derived from a stable cell line, such as a mammalian cell line.

As used herein, the term "for a period of time sufficient for the fusion protein in the dissociated complex to degrade" refers to a period of time effective to produce a measurable decrease in the amount of AHR fusion protein, which is considered directly proportional to the amount of intact AHR present in the test sample, upon treatment of a dioxin-like compound as compared to a control test without the dioxin-like compound. The period of time may vary depending upon temperature, sensitivity of the reporter system, the cell line used in the assay and other factors that may affect the measurement of the degradation of AHR. Typically, the period of time is from 30 minutes to 2 hours.

As used herein, the term "detectable signal" refers to a change in or appearance of a property in the reporter system which is capable of being perceived or sensed, either by direct observation or instrumentally, and which is a function of the presence of the fusion protein(s) in the test sample. Some examples of detectable signals are changes in visible or infrared absorption fluorescence, phosphorescence or chemiluminescence. Other examples of detectable signals may be directed to a change in electrochemical property.

In the invention, a method of detecting a dioxin-like compound in a cell-free system is provided. The method comprises:

providing a whole cell lysate derived from a cell transfected to express one or more fusion proteins fused to a reporter peptide, one of which comprises AHR fused to a reporter peptide, and wherein the whole cell lysate comprises the fusion protein in a dissociated complex;

contacting the test sample with the whole cell lysate for a period of time sufficient for the fusion protein in a dissociated complex to degrade upon the presence of the dioxin-like compound; and detecting a detectable signal generated by the reporter peptide as indicative of an amount of the fusion protein and comparing to a reference signal generated with a known concentration of a dioxin-like compound, thereby determining the presence or amount of the dioxin-like compound in the test sample.

In the invention, the cells are prepared to express a fusion protein of AHR fused to a reporter peptide, and then the whole cell lysate is obtained by lyzing the cells using any standard or commonly used method in the art. In one embodiment of the invention, the cells are prepared to co-express AHR and one or more binding partners of AHR such as HSP90, or ARNT, fused to a reporter peptide.

According to the invention, one or more binding partners other than HSP90, may be further associated to form a stable complex. As used in the invention, the binding partners other than HSP90 is selected from the group consisting of AIP, P23 and combination thereof. As shown in Example 2, one example of the cells according to the invention is the AAPA cells, which co-express AHR, AIP, P23 and ARNT; and the other example is the AAPH cells, which co-express AHR, AIP P23 and HSP90. The cell-free system for detecting dioxin-like compounds in a test sample is established by using the whole cell lysates of the cells that express AHR as prepared according to the invention, particularly the AAPA cells or the AAPH cells. Also, the methods for detecting dioxin-like compounds in a test sample using the whole cell lysates of the cells, such as the AAPA cells and the AAPH cells, are workable. In Example 3 and 4, the method for detecting 3MC or TCDD using the whole cell lysates of the AAPA cells was confirmed to be workable.

According to the invention, a dioxin-like compound in a test sample can be detected either qualitatively by comparing the detected signal with a reference signal obtained in a control test where the whole cell lysate is contacted with a test sample chemical having no effect on the AHR pathway, or quantitatively by comparing the detected signal with a standard curve plotted against known concentrations of a dioxin-like compound.

In the invention, any resonance energy transfer technique can be in conjunction with the method of the invention to enhance the sensitivity and reliability. For example, fluorescence resonance energy transfer (FRET) technique or bioluminescence resonance energy transfer (BRET) technique can be used in the invention. In one example of the invention, bioluminescence resonance energy transfer (BRET) technique was used to eliminate the necessity of using excitation illumination to initiate the fluorescence transfer as required in the fluorescence resonance energy transfer (FRET) analysis by replacing the cyan fluorescent protein (CFP) tag commonly used in FRET with a bioluminescent luciferase, such as that derived from sea pansy, *Renilla reniformis* (Xu, et al., *Proc. Natl. Acad. Sci. USA* 96(1): 151-156). It has long been regarded in the art that BRET and FRET are comparable to each other in terms of sensitivity and reliability.

According to the invention, the method in association with BRET technique could effectively enhance the sensitivity to a dioxin-like compound to picomolar level, as compared to the conventional FRET-based dioxin detection systems.

Accordingly, the invention also provides a cell-free system for performing the method for detecting a dioxin-like compound in a test sample according to the invention, comprising a whole cell lysate derived from a cell transfected to express one or more fusion proteins fused to a reporter peptide, one of which comprises an AHR, and wherein the whole cell lysate comprises the fusion protein in a dissociated complex, and a means for detecting a detectable signal generated by the reporter peptide. The method and cell-free system according to the invention provide greater time-saving and cost-effective benefits to users. In addition, the invention makes possible to establish a large-scale and high-throughput screening platform for suspected dioxin-contaminated samples.

The present invention will now be described more specifically with reference to the following examples, which are provided for the purpose of demonstration rather than limitation.

The following examples are given for the purpose of illustration only and are not intended to limit the scope of the invention.

Example 1

Plasmid Construction

Figure 1B:
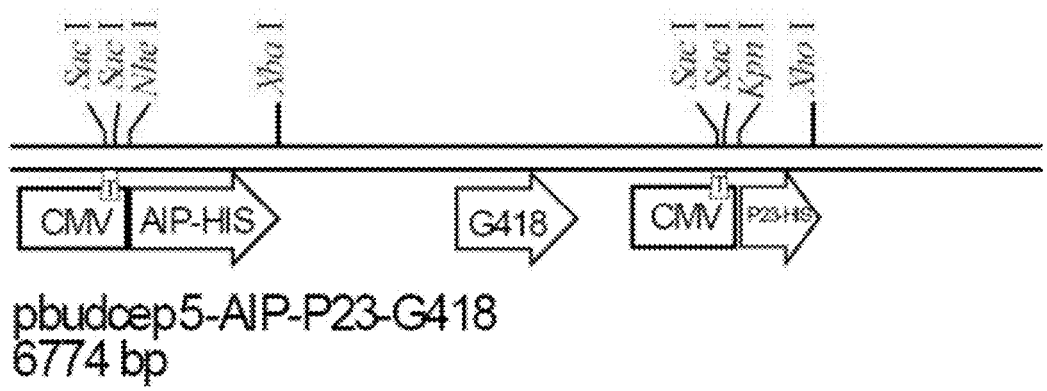
Figure 1C:
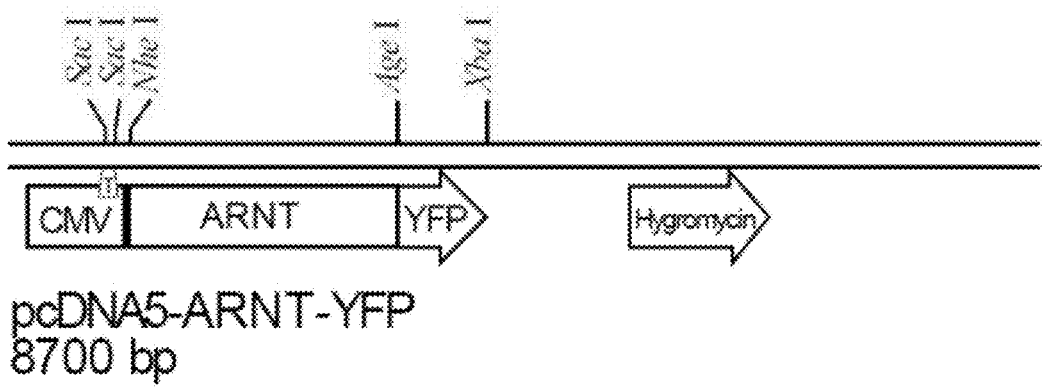
Figure 1D:
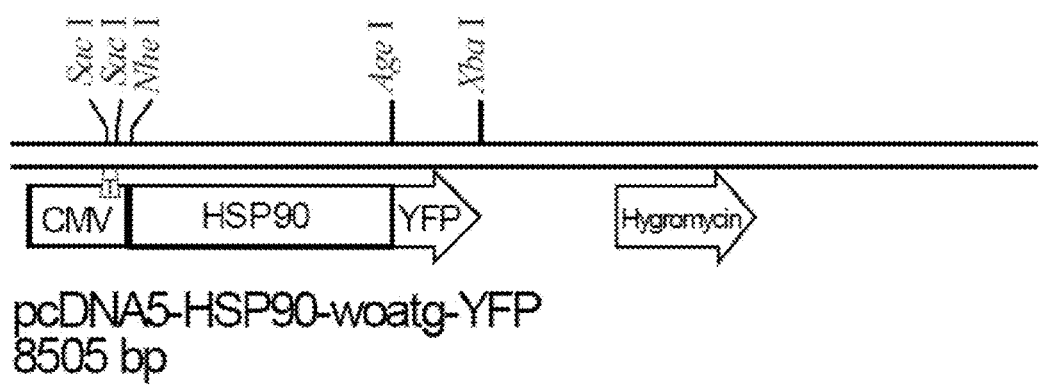

AHR (in the construction shown in FIG. 1A), AIP and P23 (in the construction shown in FIG. 1B), ARNT (in the construction shown in FIG. 1C) and HSP90 (in the construction shown in FIG. 1D) were amplified from HEK293 cDNA and all point mutations were corrected. *Renilla* Luciferase (RL) was derived from pRL-TK (Promega Corporation, Madison, Wis., USA) and YFP was from pEYFP-N1 (Clontech Laboratories, Inc., Mountain View, Calif. USA).

Example 2

Generation of Stably Transfected Cell Lines

Tetracycline-regulated expression cells (T-REx™ cells) (Invitrogen, Carlsbad, Calif., USA) were transfected with AHR-RL, AIP-HIS and P23-HIS by lipofectamin 2000™ transfection reagent (Invitrogen, Carlsbad, Calif., USA) according to the manufacturer's instructions. Transfected cells were cultured in DMEM growth medium (Gibco, USA) supplemented with 10% fetal bovine serum (FBS), (Gibco, USA), 5 µg/ml Blasticidin, 250 µg/ml Zeocin and 500 µg/ml G418. The optimal cell lines were then transfected with ARNT-YFP or HSP90-YFP and selected with 200 µg/ml Hygromycin to obtain a stable cell line transfected with ARNT-YFP (called as "AAPA cells") and obtain a stable cell line transfected with HSP90-YFP (called as "AAPH cells").

Example 3

Dioxin Detection by BRET Assay in the AAPA and AAPH Cells

Figure 2A:
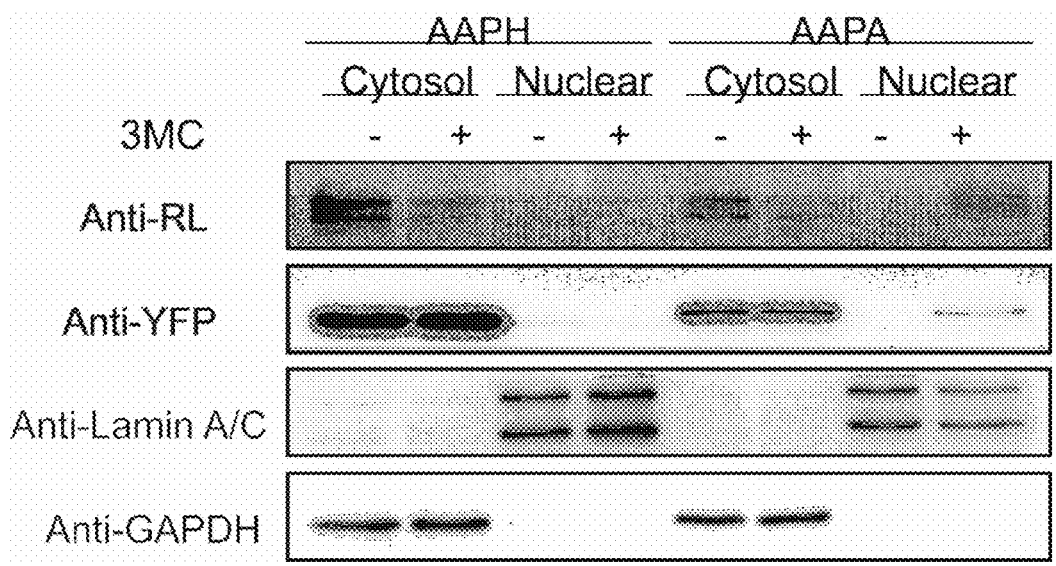
FIG. 2A shows a western blot analysis of AAPH and AAPA cells.

The AAPH and AAPA cells as obtained in Example 2 were treated with 1 µg/ml tetracycline for 24 hours and then added 10 µM 3MC for 3 hours. The expression of inducible AHR-RL, AIP-HIS (a His-tagged AIP), P23-HIS (a His-tagged P23), HSP90-YFP, or ARNT-YFP was checked by western blot. The cytosol and nuclear fractions were detected with the indicated antibodies, including anti-RL, anti-YFP, anti-Lamin A/C, and Anti-GAPDH. The results of the western blots were shown in FIG. 2A, which confirmed the AHR and ARNT protein localizations upon 3MC treatments to the AAPH and AAPA cell lines.

For the inducible protein expression and AHR complex formation, the AAPA cells, which were stably co-transfected with AHR-RL, AIP-HIS, P23-HIS and ARNT-YFP, were prepared following the method as described in Example 2 and then were treated with 1 μg/ml tetracycline for 48 hours. Then, the treated cells were washed by phosphate-buffered saline (PBS) twice.

Figure 2B:
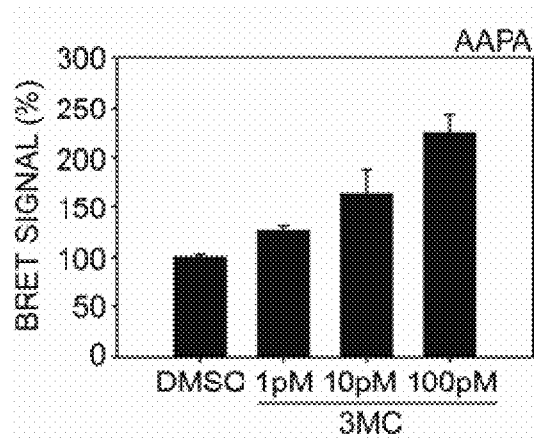
FIG. 2B shows the histogram demonstrating the relative magnitudes of BRET signals generated by adding different concentrations of 3MC to the AAPA cells.

For dioxin detection, different concentrations of 3-methyl-cholanthrene (3MC) (Boehringer Mannheim, Mannheim, Germany) were mixed with the cells and cultured in a 96-well white polystyrene plate (Corning, USA) at 37° C. for 1 hour. The BRET signals were determined by addition of coelenterazine, a substrate of *Renilla* Luciferase, to a final concentration of 0.35M. The resultant BRET signals were plotted against the concentrations of 3MC added and the results were shown in FIG. 2B. As shown in FIG. 2B, the BRET signals increased in the AAPA cells (which co-expressed AHR-RL, AIP, P23 and ARNT-YFP) in a dose-dependent manner.

Figure 2C:
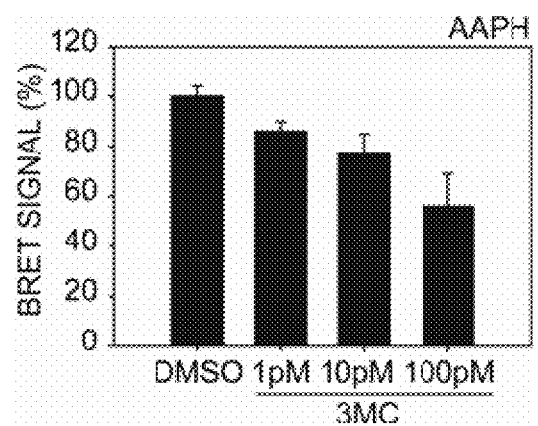
FIG. 2C shows the histogram to the AAPH cells.

On the other hand, the AAPH cells, which were stably co-transfected with AHR-RL, AIP-HIS, P23-HIS and HSP-90YFP, were prepared and then mixed with different concentrations of 3MC and cultured in a 96-well white polystyrene plate (Corning, USA) at 37° C. As shown in FIG. 2C, the BRET signals were suppressed upon 3MC treatments in the AAPH cells (which co-expressed AHR-RL, AIP-HIS, P23-HIS and HSP90-YFP) in a dose-dependent manner.

Example 4

Figure 3:
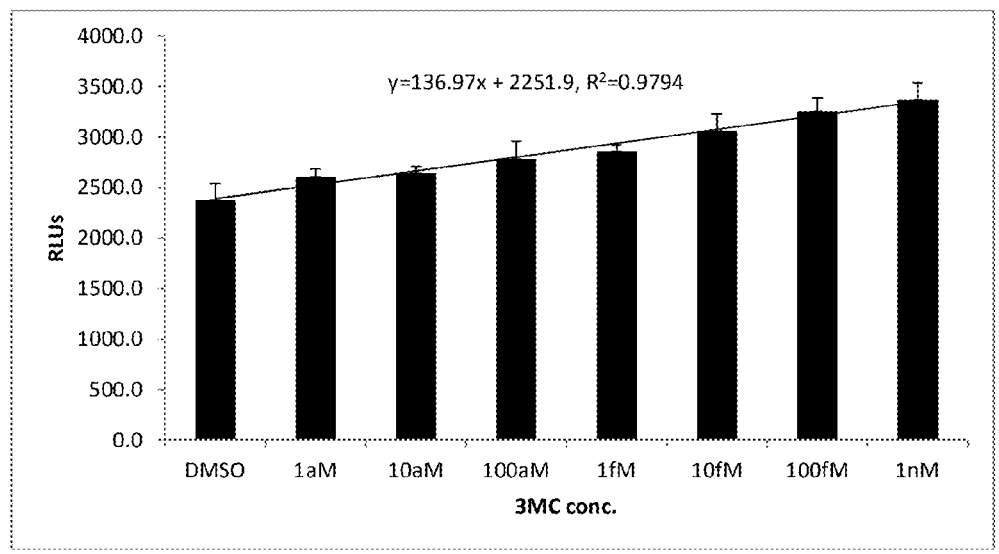
FIG. 3 is the histograms demonstrating the relative magnitudes of RL signals (RLUs) generated by adding different concentrations of TCDD to the AAPA cell lysate cultured at room temperature.

Dioxin Detection by Degradation of AHR-RL in the Cell-Free System $5 \times 10^6$ AAPA cells obtained in Example 4 were cultured in a 15 cm dish containing 25 ml DMEM medium supplemented with 10% FBS and 3.5 μg/ml tetracycline for 24 hrs. The cells were harvested and re-suspended in 10 ml cold PBS. The cells were lysed by sonication on ice using sonicator (Branson, Danbury Conn., USA) at amplitude of 10% for 30 cycles of 5 sec on and 15 sec off. The cellular debris was removed by centrifugation at 1,000 g for 10 min. For detection, 90 μl cell free lysates and different concentrations of 3MC were mixed and cultured in 96 well white polystyrene plate (Corning, USA) at room temperature. *Renilla* luciferase signals were determined by addition of coelenterazine to a final concentration of 0.35 μM. The result for detecting TCDD was shown in FIG. 3 ($y=136.97x+2251.9$, $R^2=0.9794$).

Figure 4:
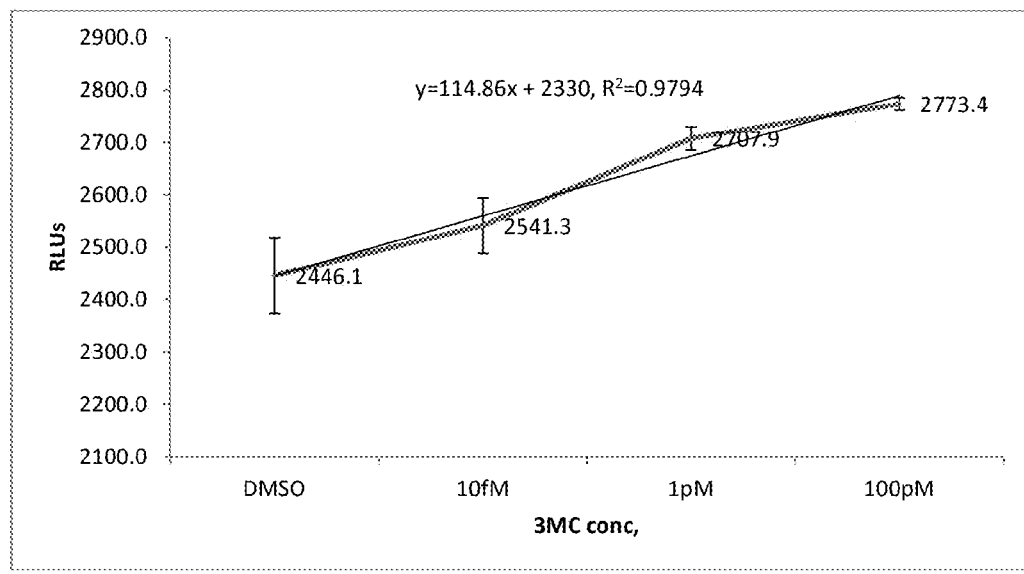
FIG. 4 is a standard curve demonstrating the relative magnitudes of RL signals (RLUs) generated by adding different concentrations of 3MC to the AAPA cell lysate at 37° C.
Figure 5:
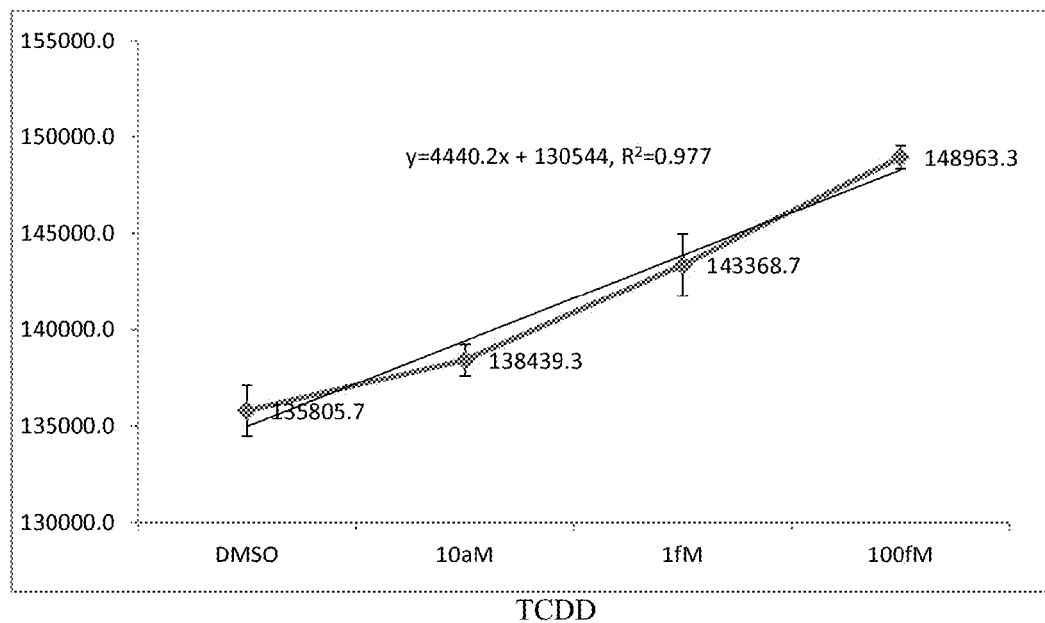
FIG. 5 is a standard curve demonstrating the relative magnitudes of RLUs generated by adding different concentrations of TCDD to the AAPA cell lysate at 37° C.

In addition, the cell free lysates and different concentrations of 3MC and TCDD were mixed and cultured in 96 well white polystyrene plate (Costar) at 37° C., respectively. The results for detecting 3MC and TCDD were shown in FIGS. 4 and 5, respectively. The results indicated that *Renilla* luciferase signals in the cell-free system increased upon 3MC or TCDD treatment in a dose-dependent manner, and the detection limits were as low as $10^{-16}$ M of 3MC or TCDD. The signals significantly increased with 3MC treatment in a dose-dependent manner ($y=114.86x+2330$, $R^2=0.9794$), see FIG. 4. Also, the signals significantly increased with TCDD treatment in a dose-dependent manner ($y=4440.2x+130544$, $R^2=0.977$), see FIG. 5. Either for the detections of 3MC and TCDD in the cell-free system had a very good correlation, and the correlation coefficients for the both detections were more than 0.95.

According to the invention, it was indicated that the 3MC- or TCDD-induced BRET signal induction was first observed with a 1-pM treatment, suggesting that the sensitivity of this detection system can reach a picomolar level. In addition, the AHR-RL signal degradation induced by 3MC or TCDD addition can be detected at a concentration as low as 10 aM. It is concluded based on the results, these BRET-based dioxin detection systems are extremely sensitive compared to the detection systems known in the art.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

I claim:

1. A method of detecting dioxin or a dioxin-like compound in a test sample, wherein the dioxin-like compound is selected from the group consisting of polychlorinated dibenzodioxins, polychlorinated dibenzofurans, and polychlorinated biphenyls, comprising:
    providing a cell-free system comprising whole cell lysates that are non-viable cell suspensions obtained by culturing a cell line transfected to co-express an aryl hydrocarbon receptor (AHR) fused to a reporter peptide, and heat shock protein 90 (HSP90) to form a complex of AHR and HSP90 in the cell line, harvesting and lysing the whole cells, and removing the cell debris;
    contacting the test sample with the whole cell lysates for a period of time sufficient to induce a change of the detectable signal generated by the reporter peptide fused to AHR when the AHR degrades upon the presence of the dioxin or dioxin-like compound; and
    detecting the change of the detectable signal of the reporter peptide fused to AHR as indicative of the level of the degradation of AHR and comparing to a reference signal-generated by the cell free system with known concentrations of dioxin or a dioxin-like compound, thereby determining the presence or amount of the dioxin or dioxin-like compound in the test sample.

2. The method of claim 1, wherein the dioxin-like compound is 2, 3, 7, 8-tetrachlorodibenzo-p-dioxin (TCDD).

3. The method of claim 1, wherein the cell line co-expresses AHR, AHR-interacting protein (AIP), P23 and HSP90.

4. The method of claim 3, wherein the cell line co-expresses AHR fused to RL, a His-tagged AIP, a His-tagged P23 and HSP90 fused to YFP.

5. The method of claim 1, wherein the reporter peptide is cyan fluorescent protein (CFP) or yellow fluorescent protein (YFP).

6. The method of claim 1, wherein the reporter peptide is a bioluminescent luciferase.

7. The method of claim 6, wherein the bioluminescent luciferase is *Renilla* luciferase (RL).

8. The method of claim 1, wherein the cell line a mammalian cell line.

9. The method of claim 1, wherein the HSP90 is fused to a reporter peptide that is different from the reporter peptide to which the AHR is fused.

* * * * *